(12) United States Patent
Ma et al.

(10) Patent No.: US 7,993,928 B2
(45) Date of Patent: Aug. 9, 2011

(54) DETECTION OF BLOOD PLASMA DANSHENSU AND SALVIANOLIC ACID B DISSIPATING BLOOD STASIS BOTANICAL

(75) Inventors: Yueming Ma, Shanghai (CN);
Tianming Wang, Shanghai (CN);
Yongyu Zhang, Shanghai (CN)

(73) Assignee: Shanghai Sundise, Shanghai (CN)

( * ) Notice: Subject to any disclaimer, the term of this patent is extended or adjusted under 35 U.S.C. 154(b) by 0 days.

(21) Appl. No.: 12/451,147

(22) PCT Filed: Apr. 28, 2008

(86) PCT No.: PCT/CN2008/000866
§ 371 (c)(1),
(2), (4) Date: Oct. 27, 2009

(87) PCT Pub. No.: WO2008/131648
PCT Pub. Date: Nov. 6, 2008

(65) Prior Publication Data
US 2010/0093099 A1    Apr. 15, 2010

(30) Foreign Application Priority Data

Apr. 27, 2007  (CN) .......................... 2007 1 0040137

(51) Int. Cl.
*G01N 33/48* (2006.01)
*G01N 33/00* (2006.01)
(52) U.S. Cl. ....................................................... 436/63
(58) Field of Classification Search ...................... 436/63
See application file for complete search history.

(56) References Cited

U.S. PATENT DOCUMENTS

| 2007/0160626 | A1 | 7/2007 | Zhang |
| 2010/0093099 | A1 | 4/2010 | Ma et al. |
| 2010/0093103 | A1 | 4/2010 | Ma et al. |
| 2010/0119541 | A1 | 5/2010 | Xu et al. |

FOREIGN PATENT DOCUMENTS

| CN | 1243743 | 2/2000 |
| CN | 99113887.2 | 8/2001 |

(Continued)

OTHER PUBLICATIONS

Luo et al., Determination of Danshensu, a major active compound of Radix *Salvia miltiorrhiza* in dog plasma by HPLC with fluorescence detection, 2001, Biomedical Chromatography, 15, 493-496.*

(Continued)

*Primary Examiner* — Christine T Mui
(74) *Attorney, Agent, or Firm* — Yunling Ren

(57) ABSTRACT

A detection method of blood plasma danshensu and salvianolic acid B of dissipating blood stasis botanical is disclosed. The method includes: (1) pretreating mammalian plasma sample: applying the plasma with medicine to small column of Waters Oasis HLB activated by methanol and water; after leaching and eluting, drying and enriching the eluent; after redissolving with mobile phase, measuring by UPLC/MS; (2) UPLC/MS measuring: UPLC condition: chromatographic column: Acquity UPLC BEH $C_{18}$, 2.1'100 mm, mobile phase A: water-acetonitrile-formic acid 95:5:0.1 v/v/v, mobile phase B: acetonitrile-formic acid 100:0.1 v/v; MS condition: electric spraying ion source (ESI), detecting with negative ion mode, scanning at the range of m/z 150-800. The method can be used for pharmacokinetics study of danshensu and salvianolic acid B in dissipating blood stasis botanical.

4 Claims, 2 Drawing Sheets

A. Danshensu; B. strengthening body resistance and dissipating blood stasis; C. blank blood plasma; D. Blood plasma of mammals taken 0.5 hours after drenched with strengthening body resistance and dissipating blood stasis botanical

FOREIGN PATENT DOCUMENTS

| CN | 1472532 | 2/2004 |
|---|---|---|
| CN | 1669573 | 9/2005 |
| CN | 02136002.2 | 9/2005 |
| CN | 1839996 | 10/2006 |
| CN | 1925864 | 3/2007 |
| CN | 1959409 | 5/2007 |
| CN | 101042380 | 9/2007 |
| CN | 2007100401416 | 9/2007 |
| CN | 101078712 | 11/2007 |
| CN | 200710040331.8 | 12/2009 |
| CN | 200510028951.0 | 3/2010 |
| JP | 1165583 | 6/1989 |
| KR | 20060038027 | 5/2006 |
| WO | 01/41778 | 6/2001 |
| WO | 2004/014409 | 2/2004 |
| WO | 2007/020382 | 2/2007 |

OTHER PUBLICATIONS

Li et al., A rapid ultra-performance liquid chromatography-electrospray ionization tandem mass spectrometric method for the qualitative and quantitative analysis of the constituents of the flower of *Trollius ledibouri* Reichb., Analytica Chimica Acta, 2006, 580, 170-180.*

Yu et al., Determination of Protocatechuic Aldehyde, Danshensu, Salvianolic Acid B and Gallic Acid in Chinese Medicine 'Shangdan' Granule by MEKC, Chromatographia, 2006, 63, 389-393.*

Liu et al., Multicenter clinical study on Fuzhenghuayu capsule against liver fibrosis due to chronic heptaitis B, Wold J Gastroenterol, 2005, 11(19), 2892-2899.*

Liu et al., Effect of fuzheng huayu recipe in treating posthepatitic cirrhosis, Liver Disease Reserch Center, Shanghai Academy of TCM, Aug. 1996, 16(8), 459-462.*

Lam et al., Salvianolic acid B, an aqueous component of danshen (*Salvia miltiorrhiza*), relaxes rat coronary artery by inhibition of calcium channels, European Journal of Pharmacology, 2006, 533, 240-245.*

Dou, et al., "Analysis of Lignans in serum of rats after oral administration of compound Wurenchun capsules by UPLC-MS/MS", Chinese Traditional Patent Medicine, Apr. 2007, vol. 29(4), pp. 550-555.

Yan, et al, "Pharmacokinetics study of schisandrin in Shengmai granule", TraiditonalChinese Drug Research & Clinical Pharmacology, Jan. 2006, vol. 17(1), pp. 36-39.

Liao, et al, "The study in situ on rat intestinal absorption of the active components in GuizhiFuling capsule", Chin. J. Nat. Med., Sep. 2005, vol. 3(5), pp. 303-307.

Xie, et al, "Determinination of anthraquinones and amygdalin in "Taohe Chengqi Decoction", by HPLC", SH. J. TCM, Jul. 2006, vol. 40(7), pp. 73-76.

Pan, et al, "Pharmacokinetics and bioavailability study of danshensu in rat", China Journal of Chinese Materia Medica, Jan. 2008, vol. 33(2), pp. 146-149.

Chen et al, "LC-MS/MS-based measurement of danshen phenolic acids in plasma", Chin. J. Clin Pharmacol Ther, Jul. 2007, vol. 12(7), pp. 748-755.

Tan, et al, "Research Concerning Influence of "Fuzheng Huayu Decoction" on Hepatocellular Apoptosis in Rats with DMN Liver Fibrosis", A Collection of Papers of the 12th National Symposium on Liver Disease with Chinese Integrative Medicine, 2003, pp. 219-223.

She, et al, "Clinical Research of Ganping Capsule Treating Liver Fibrosis in Patients with Chronic Hepatitis B", Chinese Heptology, Dec. 2002, vol. 7(4), pp. 254-255.

Lou, et al, "Comparison of schisandrin and schisandrin B in rat serum and plasma after ig Compound Wurenchun Capsules", Chinese Traditional and Herbal Drugs, vol. 37(10), Oct. 2006; pp. 1486-1489.

Xu, et al, "Determination of schizandrin in rat plasma by high-performance liquid chromatography—mass spectrometry and its application in rate pharmacokinetic studies", Journal of Chromatography B, vol. 828, 2005, pp. 55-61.

He, et al, "Analysis of lignan constituents from *Schisandra chinensis* by liquid chromatography—electrospray mass spectrometry", Journal of Chromatography A, vol. 757, 1997, pp. 81-87.

Database Biosis (Online) Biosciences Information Service, Philadelphia, PA, Feb. 2000; Baek Nam-In, et al, "Isolation of anticonvulsant compounds from the fruits of *Schizandra chinensis* Baili" Database accession No. PREV200000198785.

Churchwell, et al, "Improving LC-MS sensitivity through increases in chromatographic performance: Comparisons of UPLC-ES/MS/MS to HPLC-ES/MS/MS", Journal of Chromatography B, vol. 825, 2005, pp. 134-143.

Park, et al, "HPLC Assay and Bioequivalence Evlaution of Biphenyl Dimethyl Dicarboxylate (DDB) Products", J. Liq. Chrom, & Rel. Technol., vol. 21(12), 1998, pp. 1833-1843.

Zhao, et al, "HPLC with Column Switching Coupled to APCI-MS for Pharmacokinetic Study of Amygdalin in Rabbit Plasma", Chromatographia, vol. 65, 2007, pp. 149-153.

Kang, et al, "Micellar electrokinetic chromatography for the analysis of D-amygdalin and its epimer in apricot kernal", Journal of Chromatography A, vol. 866, 2000, pp. 253-259.

Liu, et al, "Effect of Fuzheng Huayu formula and its actions against liver fibrosis", Chinese Medicine, vol. 4(12), 2009, pp. 1-11.

Wang, et al, "Fuzheng Huayu recipe and vitamin E reverse renal interstitial fibrosis through counteracting TGF-B1-induced epithelial-to-mesenchymal transition", Journal of Ethnopharmacology, vol. 127, 2010, pp. 631-640.

Office Action dated Feb. 12, 2010 Issued by the State Intellectual Property Office of the People's Republic of China regarding Application No. 2007100403322.

U.S. Appl. No. 12/451,148, filed Oct. 27, 2009.

European Search Report regarding EP Application No. 08748426.7.

European Search Report regarding EP Application No. 08748424.2.

\* cited by examiner

A. Danshensu; B. strengthening body resistance and dissipating blood stasis; C. blank blood plasma; D. Blood plasma of mammals taken 0.5 hours after drenched with strengthening body resistance and dissipating blood stasis botanical A. Salvianolic acid B; B. strengthening body resistance and dissipating blood stasis; C. blank blood plasma; D. Blood plasma of mammals taken 0.5 hours after drenched with strengthening body resistance and dissipating blood stasis botanical

DETECTION OF BLOOD PLASMA DANSHENSU AND SALVIANOLIC ACID B DISSIPATING BLOOD STASIS BOTANICAL

CROSS REFERENCE TO RELATED APPLICATIONS

The present application is a 35 U.S.C. §371 national stage filing of International Patent Application No. PCT/CN2008/000866, filed Apr. 28, 2008, and through which priority is claimed to Chinese Patent Application No. 200710040137.X, filed Apr. 27, 2007, the disclosures of which are incorporated herein by reference in their entireties.

TECHNICAL FIELD

This invention belongs to the field of pharmacokinetics, particularly involves the detection method of strengthening body resistance and dissipating blood stasis botanical (vegetable) of blood plasma Danshensu and Salvianolic acid B.

BACKGROUND ART

Strengthening body resistance and dissipating blood stasis botanical, known as Fuzheng Huayu ("FZHY"), are composed of compound prescriptions including *salvia miltiorrhiza*, peach kernel, Schisandra chinens etc., which have the effect of curing liver, lung and kidney fibrosis; however, due to lack of pharmacokinetics research has been carried out on the strengthening body resistance and dissipating blood stasis botanical, so it is not clear about the effective ingredients in vivo, and it is difficult to provide a basis for quality control and guiding clinical rational administration, thus hinder those drugs from entering the international market.

So far, no relevant pharmacokinetic research report on strengthening body resistance and dissipating blood stasis botanical has been found, and there is not any detection method of Danshensu and Salvianolic acid B of the compound prescription in biological samples (including blood plasma sample).

Contents of the Invention

The technical matters aim to be resolved by this invention is to provide a detection method of blood plasma Danshensu and salvianolic acid B of strengthening body resistance and dissipating blood stasis botanical (vegetable), and the method is used for pharmacokinetics research, and clarifying the pharmacokinetics rules of the blood plasma Danshensu and Salvianolic acid B of the strengthening body resistance and dissipating blood stasis botanical.

The technical matters solved by this invention are achieved through the following technical solutions:

The detection method of blood plasma Danshensu and Salvianolic acid B of strengthening body resistance and dissipating blood stasis botanical (vegetable) includes the following steps:

(1) Pretreatment of Mammalian Blood Plasma Samples a. Collect mammal plasma containing drugs after being administered the strengthening body resistance and dissipating blood stasis botanical, misce bene after adding 2 to 5 mol/L phosphoric acid, and the volume ratio between the blood plasma and phosphoric acid is 1:2-3, applying the blood plasma with drugs to small column of WATERS OASIS HLB (a type of chromatographic column) activated by methanol and water; after leaching with water and 80-100% methanol and eluting with 0.2-1% ammonia-methanol, drying and enriching the eluent under the condition of 25-30° C., and redissolving the eluent with mobile phase.

b. Detection with UPLC-MS method after redissolving the eluent with the mobile phase UPLC condition: chromatographic column: ACQUITY HPLC BEH C18 (a type of chromatographic column), 2.1×100 mm, mobile phase B: water-Acetonitrile-Formic acid 95:5:0.1 v/v/v, mobile phase B: Acetonitrile-Formic acid 100:0.1 v/v; MS condition: electrospray ionization(ESI) ion source, detecting with negative ion mode, and mass scanning at the range of m/z 150 to 800.

The leaching conditions in the described step (1) are use water for the first step, and use 80-100% methanol for the second step, and eluting conditions are: 0.2-1% ammonia-methanol.

The described step (2) detects with negative ion mode, the desolvation gas flow is 440 L/h, the desolvation gas temperature is 300° C., the cone gas flow is 50 L/h, the ion source temperature is 100° C., the spray capillary voltage is 3800 V, the sampling cone voltage is 30V, the extracting cone voltage is 2.00 V, the lens voltage is 0.1 V.

In solid-phase extraction process of this invention, the adsorption capacity of the solid phase to the analytes is greater than the sample mother liquor, when the samples pass through the solid-phase extraction column, the analytes and a number of similar ingredients were adsorbed on the surface of solid, and other ingredients then pass through the column with the sample mother liquor, first leach columns with larger polar solvents, to rinse and remove a number of unrelated ingredients, and finally elute the analytes with appropriate solvent, drain and enrich the eluent; use UPLC system, separate the analytes with other ingredients in the elution, and finally detected with mass spectrometry detector.

The Danshensu and Salvianolic acid B in this invention are both water-soluble ingredients, using solid-phase extraction method, can fully extract the Danshensu and salvianolic acid B in the stereoplasm, combined with using a UPLC/MS system to detect, markedly improve the resolutions of Danshensu and salvianolic acid B among other ingredients in the samples, and the analysis method is more sensitive and faster, to facilitate the detection of the blood plasma concentration of the Danshensu and salvianolic acid B in pharmacokinetic research.

MODE OF CARRYING OUT THE INVENTION

Combining with the specific embodiments, further elaboration of this invention is given below. It should be understood that these embodiments are only for description of the present invention but not the use of limiting the scope of the present invention. It should also be understood, after reading the contents taught in this invention, technicians in this field can make various changes or modification to this invention, these equivalent forms are all included in the scope defined by the claims attached to this application.

Embodiment 1

The detection method of blood plasma Danshensu and Salvianolic acid B of strengthening body resistance and dissipating blood stasis botanical includes:

1. Method of pretreating mammalian blood plasma sample: Collect mammal plasma containing drugs 0.5 hours after being administered the strengthening body resistance and dissipating blood stasis botanical, misce bene after adding 2-5 mol/L phosphoric acid, and the volume ratio between the blood plasma and phosphoric acid is 1:2-3, applying the blood plasma with drugs to small column of WATERS OASIS HLB (a type of chromatographic column) activated by methanol and water; after leaching with water and 80-100% methanol and eluting with 0.2-1% ammonia-methanol, drying and enriching the eluent under the condition of 25-30° C., and redissolving the eluent with mobile phase.

2. UPLC/MS detection method: The analysis conditions of the applied UPLC/MS method in this invention, UPLC condition: chromatographic column: ACQUITY HPLC BEH C18 (a type of chromatographic column), 2.1×100 mm, mobile phase A: Water-Acetonitrile-Formic acid 95:5:0.1 v/v/v, mobile phase B: Acetonitrile-Formic acid 100:0.1 v/v, eluting in accordance with the following gradient:

| Time(min) | Flow Rate (mL/min) | % A | % B |
|---|---|---|---|
| 0 | 0.300 | 100 | 0 |
| 5.00 | 0.300 | 85.0 | 15.0 |
| 10.00 | 0.300 | 70.0 | 30.0 |
| 20.00 | 0.300 | 40.0 | 60.0 |
| 30.00 | 0.300 | 20.0 | 80.0 |
| 35.00 | 0.300 | 20.0 | 80.0 |
| 35.01 | 0.300 | 100.0 | 0.0 |
| 38.00 | 0.300 | 100.0 | 0.0 |

MS conditions: electrospray ionization (ESI) ion source, detecting with negative ion mode, the desolation gas flow is 440 L/h, the desolation gas temperature is 300° C., the cone gas flow is 50 L/h, the ion source temperature is 100° C., the spray capillary voltage is 3800 V, the sampling cone voltage is 30V, the extracting cone voltage is 2.00 V, the lens voltage is 0.1 V, and mass scanning at the range of m/z 150-800.

Figure 1:
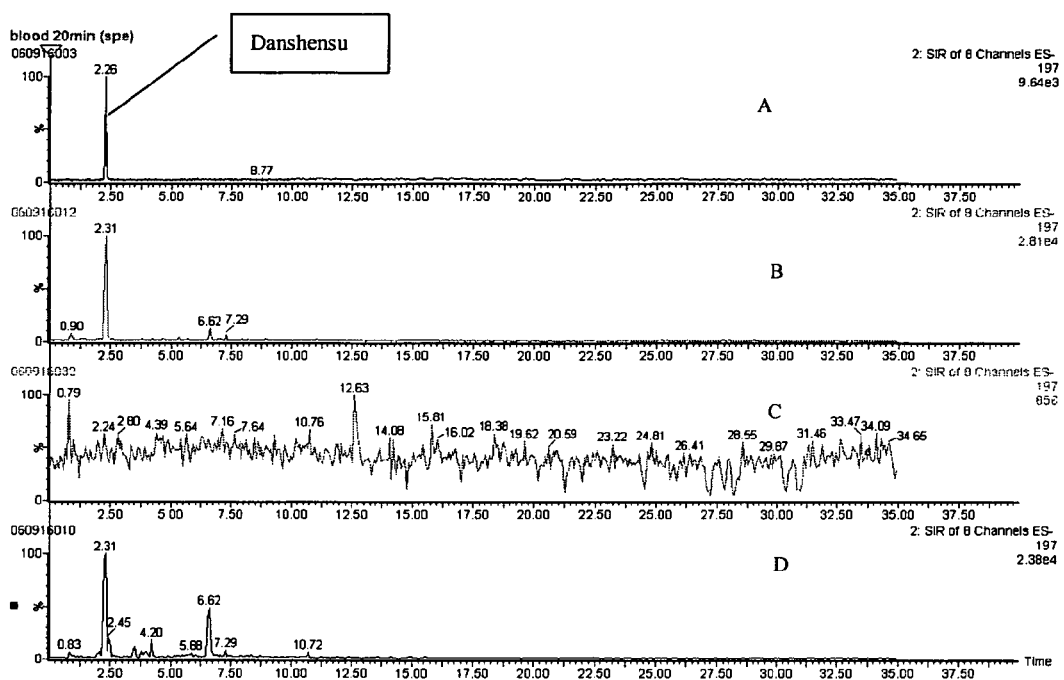
FIG. 1. UPLC-MS chromatogram of Danshensu.
Figure 2:
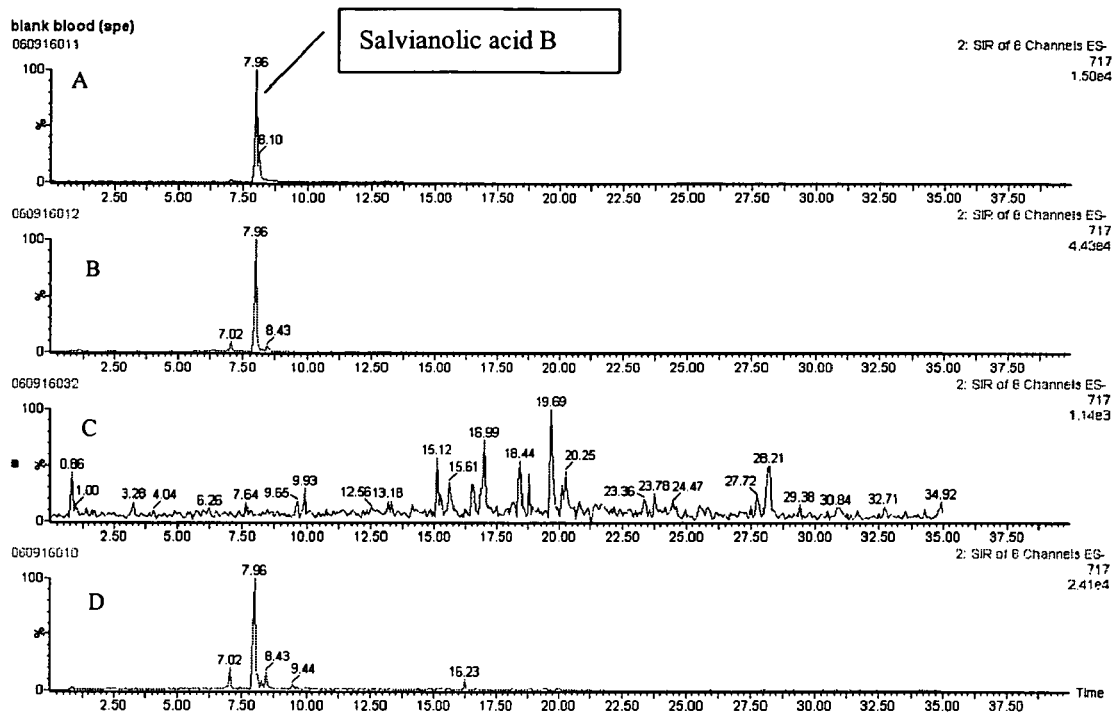
FIG. 2. UPLC-MS chromatogram of Salvianolic acid B.

Detection results: Danshensu and Salvianolic acid B can be detected in the blood plasma of mammals after drenched with strengthening body resistance and dissipating blood stasis botanical (see FIG. 1-2).

The invention claimed is:

1. A method for detecting the presence of Danshensu and salvianolic acid B in the blood plasma of an animal after administering the botanical extract composition Strengthening Body Resistance and Dissipating Blood Stasis Botanical to said animal, comprising the steps of:
   a. collecting the blood plasma from said animal 0.5 hours after administration of Strengthening Body Resistance and Dissipating Blood Stasis Botanical to said animal;
   b. adding 2-5 mol/L of phosphoric acid to said blood plasma to form a blood plasma solution at a ratio (v/v) of blood plasma:phosphoric acid equals to 1: 2-3;
   c. apply said blood plasma solution to a chromatography column, wherein said column is activated by methanol and water prior to applying said blood plasma solution;
   d. washing said column with water and 80-100% methanol;
   e. eluting said column with 0.2-1% methanol in ammonia to obtain an eluent;
   f. drying said eluent at 25-30° to obtain a dried eluent;
   g. redissolving said dried eluent in a mobile phase solution comprising a mobile phase A and a mobile phase B at a ratio of 80 (mobile phase A)/20 (mobile phase B) to form a redissolved eluent, wherein said mobile phase A comprises water, acetonitrile, and formic acid at a ratio (v/v/v) of water/acetonitrile/formic acid equals to 95/5/0.1 and said mobile phase B comprises acetonitrile and formic acid at a ratio (v/v/v) of acetonitrile/formic acid equals to 100/0.1;
   h. preparing conditions for detection by ultra performance liquid chromatography electrospray ionization tandem mass spectrometry (HPLC/MS/ESI), wherein the ultra performance liquid chromatography (HPLC) conditions comprise a 2.1×100 mm chromatography column, said mobile phase A, and said mobile phase B; and wherein the mass spectrometry (MS) conditions comprise electrospray ionization (ESI) ion source in a negative ion mode; and
   i. detecting the presence of Danshensu and salvianolic acid B in said redissolved eluent under the conditions in step h at a mass scan range of m/z 150-800.

2. The method in claim 1, wherein said detection of the presence of Danshensu and salvianolic acid B is performed under the conditions having a desolvation gas flow at 440 L/h, a desolvation gas temperature at 300° C., the cone gas flow at 50 L/h, an ion source temperature at 100° C., a spray capillary voltage at 3800 V, a sampling cone voltage at 30 V, an extracting cone voltage at 2.00 V, a lens voltage at 0.1 V.

3. The method in claim 1, wherein said column in step d is washed first with water followed by 80-100% methanol.

4. A method for detecting the presence of Danshensu and salvianolic acid B in the blood plasma of an animal after administering the botanical extract composition Strengthening Body Resistance and Dissipating Blood Stasis Botanical to said animal, comprising the steps of:
   a. collecting the blood plasma from said animal 0.5 hours after administration of Strengthening Body Resistance and Dissipating Blood Stasis Botanical to said animal;
   b. adding phosphoric acid to said blood plasma to form a blood plasma solution;
   c. applying said blood plasma solution to a chromatography column;
   d. washing said column with water and methanol;
   e. eluting said column to obtain an eluent;
   f. drying said eluent to obtain a direct eluent;
   g. redissolving said dried eluent in a solution for detection by ultra performance liquid chromatography-electrospray ionization tandem mass spectrometry (HPLC/MS/ESI);
   h. preparing conditions for said HPLC/MS/ESI; and
   i. detecting the presence of Danshensu and salvianolic acid B in said redissolved eluent.

* * * * *